United States Patent
Shukla et al.

(10) Patent No.: US 7,276,158 B1
(45) Date of Patent: Oct. 2, 2007

(54) INCISION-BASED FILTRATION/SEPARATION PIPETTE TIP

(76) Inventors: Ashok K Shukla, 10423 Popkins Ct., Woodstock, MD (US) 21163; Mukta M. Shukla, 10423 Popkins Ct., Woodstock, MD (US) 21163; Amita M Shukla, 10423 Popkins Ct., Woodstock, MD (US) 21163

( * ) Notice: Subject to any disclaimer, the term of this patent is extended or adjusted under 35 U.S.C. 154(b) by 806 days.

(21) Appl. No.: 09/591,009

(22) Filed: Jun. 9, 2000

(51) Int. Cl.
*B01D 15/08* (2006.01)

(52) U.S. Cl. .................. 210/198.2; 210/635; 210/656; 422/70; 422/100; 422/101

(58) Field of Classification Search ............ 210/198.2, 210/289, 291, 497.1, 497.3, 498, 485; 422/70, 422/100, 101
See application file for complete search history.

(56) References Cited

U.S. PATENT DOCUMENTS

| | | | | |
|---|---|---|---|---|
| 975,874 A * | 11/1910 | Korn | ................... | 210/484 |
| 3,398,836 A * | 8/1968 | Hugentobler | .............. | 210/455 |
| 3,478,886 A * | 11/1969 | Hornbeck | ............... | 210/198.2 |
| 4,341,635 A * | 7/1982 | Golias | .................. | 210/656 |
| 4,405,344 A * | 9/1983 | Sisti | ..................... | 95/82 |
| 4,526,686 A * | 7/1985 | Sisti | .................... | 210/198.2 |
| 4,766,082 A * | 8/1988 | D'Autry | ................. | 436/178 |
| 4,787,971 A * | 11/1988 | Donald | .................. | 210/198.2 |
| 4,787,973 A * | 11/1988 | Ando et al. | .............. | 210/282 |
| 4,792,399 A * | 12/1988 | Haney et al. | ............. | 210/484 |
| 4,832,916 A * | 5/1989 | Gilak | ................... | 422/70 |
| 4,863,610 A * | 9/1989 | Campbell | ................ | 210/658 |
| 5,019,270 A * | 5/1991 | Afeyan et al. | ............. | 210/656 |
| 5,169,528 A * | 12/1992 | Karbachsch et al. | ......... | 210/264 |
| 5,266,193 A * | 11/1993 | Kimura | .................. | 210/198.2 |
| 5,316,732 A * | 5/1994 | Golukhov | ................ | 422/102 |
| 5,395,521 A * | 3/1995 | Jagadeeswaran | ......... | 210/198.2 |
| 5,413,708 A * | 5/1995 | Huse | ..................... | 210/198.2 |
| 5,589,063 A * | 12/1996 | Sanford | .................. | 210/198.2 |
| 5,882,521 A * | 3/1999 | Bouvier | .................. | 210/635 |
| 5,997,746 A * | 12/1999 | Valaskovic | ............... | 210/656 |
| 6,048,457 A * | 4/2000 | Kopaciewicz et al. | ... | 210/321.6 |
| 6,136,187 A * | 10/2000 | Zare | ..................... | 210/198.2 |
| 6,190,559 B1 * | 2/2001 | Valaskovic | ............... | 210/656 |
| 6,566,145 B2 * | 5/2003 | Brewer | .................. | 436/178 |
| 2004/0052689 A1 * | 3/2004 | Yao | ..................... | 422/100 |

* cited by examiner

Primary Examiner—Ernest G. Therkorn

(57) ABSTRACT

This invention relates to a pipette tip designed to perform filtration or sample separation on the basis of one or more perforations, holes or incisions performed on the tip. Such perforation, holes or incisions are large enough to permit the passage of fluids or smaller particles, but small enough to block the passage of solid materials or larger particles, such as those including chromatography media. Such a pipette tip can thus be used for the filtration or separation of samples without the use of a filter, secondary solid matrix or any other components needed to hold chromatography media and other solid matrices within the pipette tip during the separation process.

11 Claims, 4 Drawing Sheets

INCISION-BASED FILTRATION/SEPARATION PIPETTE TIP

FIELD OF THE INVENTION

This invention relates to a pipette tip designed to perform filtration or sample separation on the basis of one or more perforations, holes or incisions performed on the tip. Such perforations, holes or incisions are large enough to permit the passage of fluids or smaller particles, but small enough to block the passage of solid materials or larger particles, such as those comprising chromatography media. Such a pipette tip can thus be used for the filtration or separation of samples without the use of a filter, secondary solid matrix or any other components needed to hold chromatography media and other solid matrices within the pipette tip during the separation process. The device described herein can be used for sample separation or purification using a vacuum, pressure, centrifugation, gravitation or other separation methods. The desired sample, containing bio-molecules such as DNA, proteins or other molecular components, is passed through the perforations, cuts or slits in said device during the separation process.

BACKGROUND OF THE INVENTION

Although a spectrum of analytical methods for small sample separation and purification have been developed, a number of problems, such as the slow speed of the separation process and the loss of sample volume, limits the quality of currently available methods. In the present invention, we describe the use of a pipette tip, which has one or more perforations, incisions, or holes in the tip, designed for sample filtration or separation. The perforations, holes or incisions are of such dimensions that fluids and smaller particles can pass through them while larger particles are retained in said pipette tip. The application of such a device is useful for performing sample separation and filtration with or without chromatography and other separation media because it eliminates the need to place a filter or secondary solid matrices into the tip to retain said chromatography and other separation media within the tip during sample preparation. Depending on the specifications of the chromatography material, selected molecules from the sample can be separated or purified by binding to, or by being entrapped in, said material. The bound molecules can later be eluted from said chromatography material by the use of different solvents.

Filters and secondary solid matrices are traditionally used in separation columns, such as pipette tips, to retain the solid matrix or column material in said pipette tips or columns, while letting fluids and desired sample components flow through. Currently available sample preparation pipette tips rely on filters and secondary solid support matrices to hold chromatography and separation media in the tip while permitting selective components of the sample to pass through the lower end of the tip. The filters used in such devices may be made of silica, polypropylene, nylon, polytetrafluoroethylene or any other inert materials that do not react with the elution solution. The pore size of the filter material is smaller than the particle size of the solid matrix or chromatography material placed above it so that the solid matrix or chromatography material is retained in the tip.

In pipette tips, or other separation/chromatography columns using filters, sample separation can be performed by centrifugation, gravitation, vacuum suction, pressure application or by syringe- or pipette-based sample delivery through the tip or column. Such methods are used for the separation and purification of small sample volumes of bio-molecules such as proteins, peptides and DNA. The solid matrix or column material can consist of any material such as gel-filtration, affinity, ion-exchange, reverse-phase, and silica or modified-silica materials.

When sample volumes in the micro liter range are separated using currently available pipette tips and other separation/chromatography columns, one of the commonly associated problems is sample loss during the separation process due to the retention of sample components on the filter or in the solid support matrix. Since the concentration of bio-molecules in micro volume samples is so small, the retention of molecules in the filter or secondary solid matrix can result in significant loss of the total sample volume. Also, since the volume of the filter or solid support matrix is often as large as the volume of the micro volume sample itself, the separation or chromatography process is adversely affected due to the large volume of the filter or solid support material through which the sample must pass during the separation process. The filter or solid support material may also absorb proteins or bio-molecules from the sample, resulting in lower than desired sample recovery.

Also, the filter material and solid matrix or column material may behave differently in different elution media, subsequently interfering with both the quality of the separation process and the volume of the sample retained. Furthermore, the presence of the filter material slows down the sample separation process because the sample is first passed through the column material and then the filter prior to the completion of sample separation. Additionally, the structure and design of many micro pipette tips, intended for micro-liter sample volumes, are not well suited to the addition of filters or secondary solid matrices into the tip.

The invention described and claimed herein comprises a pipette tip designed to perform filtration or sample separation on the basis of one or more perforations, incisions or holes performed on the tip for sample filtration or separation. The perforations, holes or incisions are of such dimensions that fluids and smaller particles can pass through them while larger particles are retained in said pipette tip. During the process of sample separation, performed by centrifugation, gravitation, vacuum suction, pressure application or by syringe-based sample delivery through the pipette tip described herein, the filter solid support matrix or column material is retained in said pipette tip while selected sample components pass through said perforation or incision.

The features of the present invention eliminate the need for filters or solid support matrices at the lower end of the pipette tip to support the chromatography material during sample separation. Thus, the present invention, as described herein, will result in higher sample recovery due to the absence of sample retention on a filter or solid support matrix. The present invention will also eliminate separation problems associated with filter materials and solid support matrices interacting differently with alternate elution media, thus improving the quality of sample separation. The present invention also leads to more rapid sample preparation since the sample does not flow through a filter or solid support matrices as part of the separation process. Filters and solid support matrices reduce the rate of sample flow.

The various features of novelty, which characterize the invention, are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWINGS

The foregoing and still other objects of this invention will become apparent, along with various advantages and features of novelty residing in the present embodiments, from study of the following drawings, in which.

DESCRIPTION OF THE PREFERRED EMBODIMENTS

Figure 1:
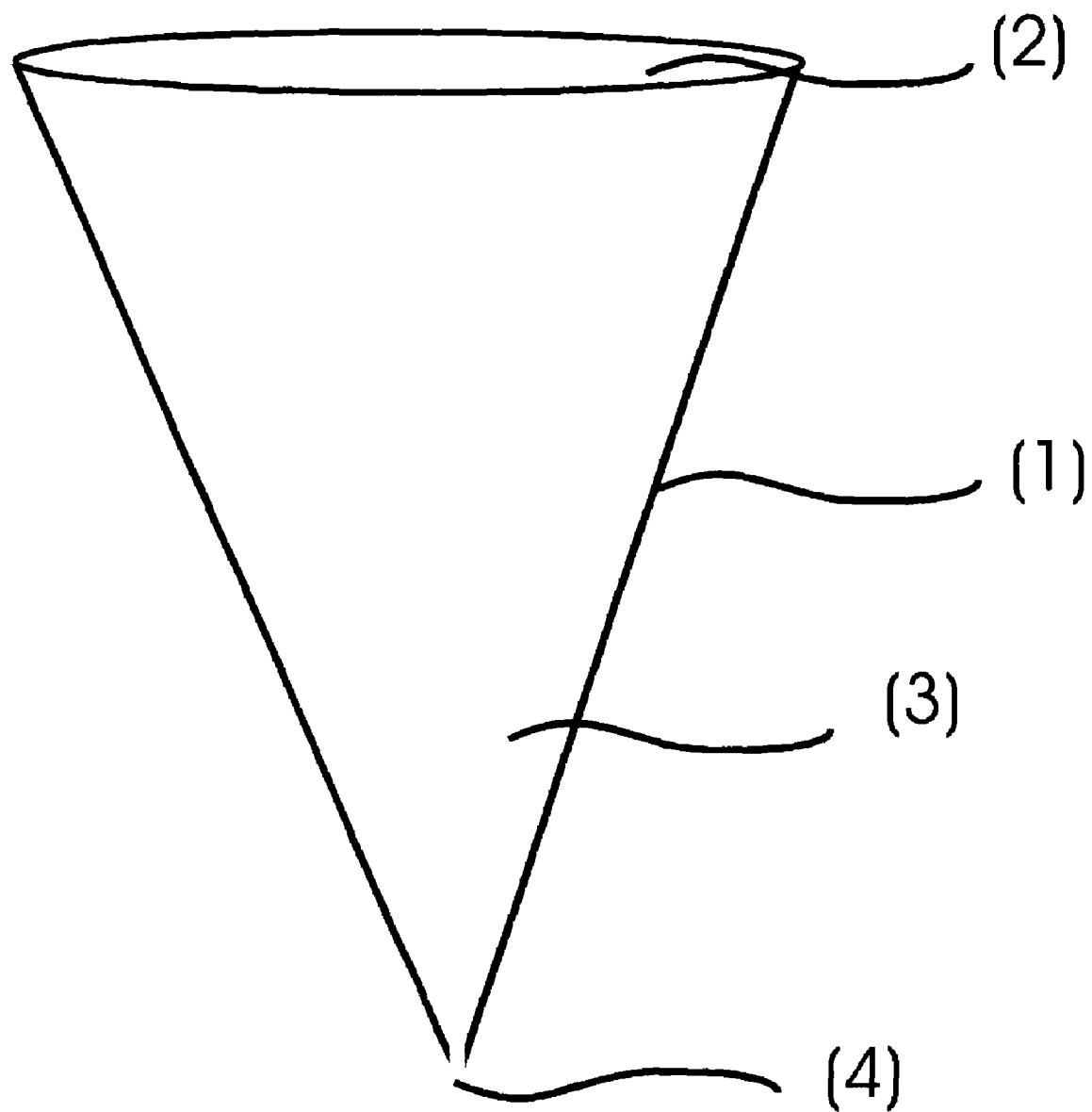
FIG. 1 is an expanded view of one embodiment of the pipette tip, according to the present invention.

Referring to the drawings, FIG. 1 is an expanded view of one embodiment of the pipette tip (1), according to the present invention. The pipette tip (1), has an upper end (2) and a lower end (3). The lower end contains one or more perforations or incisions (4) designed to permit the selective passage of smaller particles or fluids through said perforations or incisions (4) while retaining larger particles in said tip (1). Said pipette tip (1) can be any type of holding unit such as a tube, housing, column, vial or any other type of holding unit suited to the sample preparation process. Said pipette tip (1) can be of any shape or size and both the upper end (2) and lower end (3) may be closed or open ends. Said pipette tip (1) can be made of one or more natural or synthetic materials including but not limited to polymers such as polytetrafluoroethylene, polypropylene, polyethylene, fluoropolymers (e.g. FEP), polysulfone, polyethersulfone, cellulose acetate, polystyrene, polystyrene/acrylonitrile copolymer, PVDF, and glass. Said pipette tip (1) can have a volume anywhere from 0.00001 to 100 milliliters.

Figure 2:
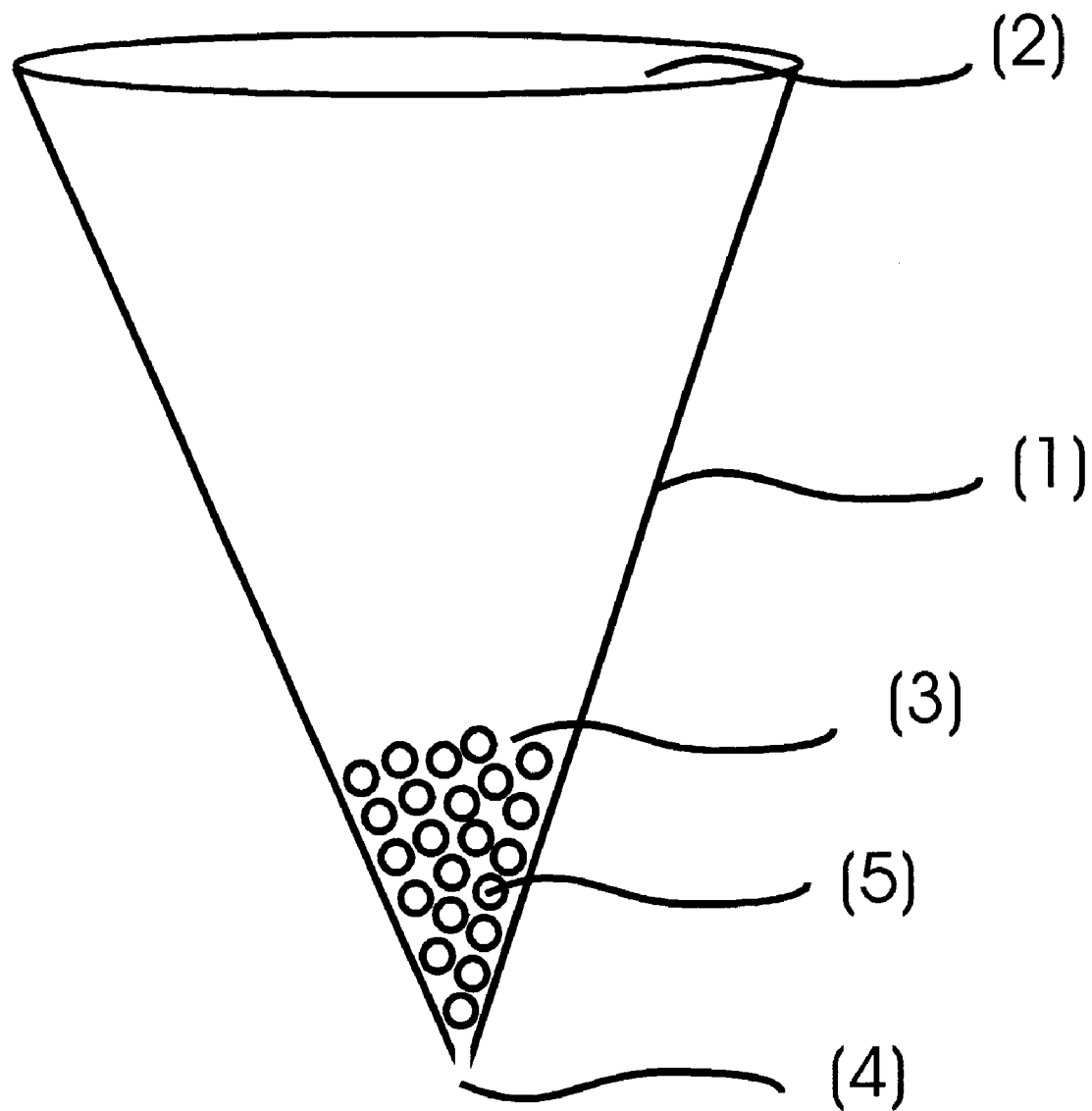
FIG. 2 is an expanded view of one embodiment of the pipette tip, according to the present invention, containing a chromatography material within it.

FIG. 2 is an expanded view of one embodiment of the pipette tip (1), according to the present invention, containing a chromatography material (5) within it. Said chromatography material can consist of one or more different types of chromatography or separation media including, but not limited to, chromatography silica, polystyrene, carbon, polymers, media, gels, bacteria, living cells, solid powders or any other media used for the purposes of sample filtration, separation or purification. The chromatography material (5) can also be composed of non-silica, polymer-based, active charcoal, zirconium, titanium or other materials.

The chromatography material (5) can also be a mix of materials with different particle sizes or different types of materials such as cation and anion exchange materials, affinity materials, and normal phase or reverse phase materials. Said chromatography or separation material (5) can be in any shape or form including but not limited to particle form, powder form, sheet form, woven, and non-woven form or in any other physical configuration suited to the design of the pipette tip and the experimental conditions. Furthermore, the particles of said chromatography or separation material (5) can be chemically or physically modified and may be porous or non-porous. The sizes of the inert or chromatography material particles can be from nanometers to micrometers.

Said chromatography or separation material (5) can be held within said pipette tip (1) through the use of a disc, filter or any other means suitable to the application. The passage of the sample through the pipette tip (1) can be performed using any relevant methods, including but not limited to, centrifugation, gravitation, vacuum suction, pressure application or syringe-based sample delivery through said pipette tip. The sample components passed through the perforations/incisions (4) of the pipette tip (1) can be collected in any sample collection tube. The sample can be introduced into said pipette tip (1) either through placement of the sample through said upper end (2) or suction of the sample through said lower end (3).

Figure 3:
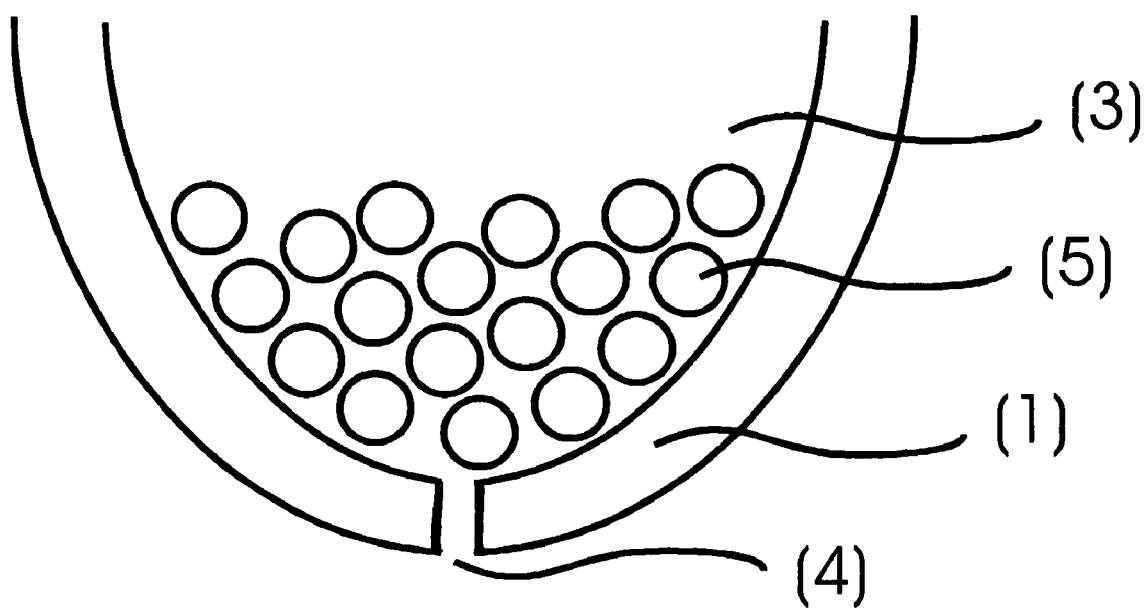
FIG. 3 is an expanded view of one embodiment of a vertical cross-section of a incision/perforation at the bottom of the pipette tip, according to the present invention.
Figure 4:
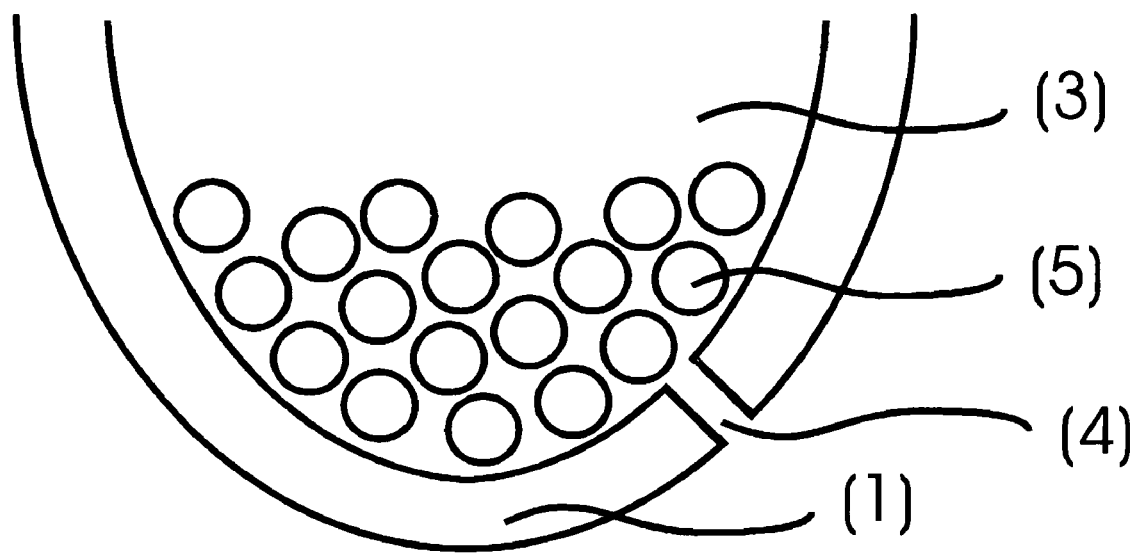
FIG. 4 is an expanded view of one embodiment of a vertical cross-section of a incision/perforation on the lateral side of the pipette tip, according to the present invention.

FIG. 3 is an expanded view of one embodiment of a vertical cross-section of a incision/perforation (4) at the bottom of the pipette tip (1), according to the present invention. FIG. 4 is an expanded view of one embodiment of a vertical cross-section of a incision/perforation (4) on the lateral side of the pipette tip (1), according to the present invention. As is shown in FIGS. 3 and 4, the chromatography material particles (5) are of such a shape and size that they will not be able to pass through the incision/perforation (4) in said pipette tip (1). Thus, during the process of sample separation performed by centrifugation, gravitation, vacuum suction, pressure application or by syringe-based sample delivery through the pipette tip described herein, the chromatography or separation material is retained in said pipette tip. Any other applicable methods can also be used to perform sample preparation and separation.

The incisions/perforations (4) can be made at the bottom tip or on the lateral sides of said lower end (3) of said pipette tip (1). The lower end (3) of said pipette tip (1) may have one or more incisions/perforations (4). The perforations/incisions can be any type of perforation or incision including, but not limited to, cracks, slits, cuts, holes, and orifices. The incisions/perforations (4) can be made by any chemical or physical methods, including but not limited to, cutting with a knife, blade, or laser beam, applying heat or pressure, using chemical reactions, or using any other method that can be used to perforate, cut or crack the lower end of said pipette tip to permit the selective passage of particles or molecules through said lower end.

The incisions/perforations (4) can also be made through the use of a laser beam or other means not requiring direct physical contact between the perforating or incision-making device and the pipette tip (1) described in the present invention. The perforations or incisions (4) may be of any shape or size, depending on the specifications of said pipette tip (1), but are intended so as to permit the selective passage of materials through the lower end (3) of said pipette tip (1). Furthermore, the incisions/perforations (4) can be made during the molding process through which the pipette tip (1) is formed.

Multiple units of the pipette tip (1), according to the present invention, can be joined together to develop a system for the simultaneous preparation of multiple samples. Said pipette tips (1) can be joined together in any type of configuration including but not limited to 2-unit, 8-unit, 48-unit, 96-unit, 384-unit or 1536-unit formats. The pipette tip (1) either as a single unit or in the multi-unit system, can be combined with a piston or similar device designed to pull the sample into the tip or push the sample out of the tip to perform sample preparation. The sample can be introduced into or removed from the interior of said pipette tip (1) through any automatic (e.g. robotic) or manual methods relevant to the application.

The pipette tip described in the present invention has many small sample preparation, filtration and purification applications including but not limited to high throughput screening and the purification of DNA, proteins, peptides, lipids, carbohydrates, vitamins and other chemicals and bio-molecules. Separation of sample components can be based on size, chemical properties or physical properties of the sample's component molecules and particles. Samples purified by these methods can be used for further analysis, through mass spectrometry, High Performance Liquid Chromatography (HPLC), electrophoresis, capillary electrophoresis, NMR, enzyme assays, protein binding assays and other chemical or biochemical reactions.

The broader usefulness of the invention may be illustrated by the following examples.

EXAMPLE #1

Use of the Present Invention for Peptide Sample Preparation

In this experiment, we used a 10–200 micro-liter micro pipette tip that was closed at its bottom end. An incision with approximate dimensions of 2 to 4 milli-meters in length, and 10 microns in width was made at the bottom end of the tip, using a sharp blade to create the incision. A 50 micro-liter slurry of C-18 column material (with particle sizes of 40–60 microns) was introduced into the tip through the top open end. The tip was attached to a pipette and pressure was applied through the pipette. The column material settled at the bottom of the pipette tip while the slurry water flowed through the slit.

A 20 micro-liter peptide solution containing buffer was pipetted on top of the C-18 column material bed in the pipette tip. Pressure was applied through the pipette and the sample fraction passing through the slit in the tip was collected in a separate collection tube. The peptide was retained in the tip while water and impurities passed through the incision. The column was washed with 20 micro-liters of water a few times and the peptide was then eluted from the column using 50 percent isopropanol. The purified peptide sample was then analyzed by HPLC.

While a specific embodiment of the invention has been shown and described in detail to illustrate the application of the principles of the invention, it is understood that the invention may be embodied otherwise without departing from such principles and that various modifications, alternate constructions, and equivalents will occur to those skilled in the area given the benefit of this disclosure and the embodiment described herein, as defined by the appended claims.

What is claimed is:

1. A pipette tip for sample preparation, which contains chromatography particles and has an open upper end and a closed lower end and has one or more slits at said lower end to permit the passage of fluids through said slits while retaining said chromatographic particles in said pipette tip, said slits having a length to width ratio of 200:1 to 400:1, a ratio of chromatographic particle diameter to slit width ratio 4:1–6:1, and a ratio of chromatographic particle diameter to slit length 1:33.33 to 1:100.

2. A pipette tip, as in claim 1, wherein said pipette Tip is a holding unit is selected from the group consisting of a tube, a housing, a column, and a vial.

3. A pipette tip, as in claim 1, wherein multiple units of said pipette tip are joined together.

4. A pipette tip, as in claim 1, wherein said pipette tip is made of materials selected from the group consisting of polytetrafluoroethylene, polysulfone, polyethersulfone, polypropylene, polyethylene, fluoropolymers, cellulose acetate, polystyrene, polystyrene/acrylonitrile copolymer, PVDF, glass, and combination thereof.

5. A pipette tip as in claim 1, wherein the volume of said pipette tip is between 0.00001 and 100 milliliters.

6. A pipette tip as in claim 1, wherein one or more of said slits are made at the bottom of or on the lateral sides of said pipette tip.

7. A pipette tip as in claim 1, wherein the method to make said perforations is a chemical or physical method selected from the group consisting of cutting with a knife, blade, or laser beam, applying heat or pressure, using chemical reactions, and combination thereof.

8. A pipette tip as in claim 1, wherein said chromatographic particles is selected from the group consisting of one type of material, a mixture of different sizes of particles, different types of materials, and combination thereof.

9. A pipette tip as in claim 1, wherein said chromatography particles is selected from the group consisting of chromatographic silica, polystyrene, carbon, polymers, media, gels, solid powders, media used for the purposes of sample filtration, separation or purification.

10. A pipette tip as in claim 1, wherein said chromatography particles can be chemically or physically modified to alter the nature of the separation process.

11. A pipette tip as in claim 1 wherein said pipette tip is combined with a piston designed to pull the sample into said pipette tip or push said sample out of said pipette tip.

* * * * *